(12) United States Patent
Carlson et al.

(10) Patent No.: US 6,748,272 B2
(45) Date of Patent: Jun. 8, 2004

(54) ATRIAL INTERVAL BASED HEART RATE VARIABILITY DIAGNOSTIC FOR CARDIAC RHYTHM MANAGEMENT SYSTEM

(75) Inventors: Gerrard M. Carlson, Champlin, MN (US); Kenneth L. Baker, Shoreview, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 263 days.

(21) Appl. No.: 09/861,017

(22) Filed: May 18, 2001

(65) Prior Publication Data

US 2002/0128564 A1 Sep. 12, 2002

Related U.S. Application Data

(63) Continuation-in-part of application No. 09/802,316, filed on Mar. 8, 2001, now Pat. No. 6,678,547.

(51) Int. Cl.⁷ .............................................. A61N 1/365
(52) U.S. Cl. ............................. 607/14; 607/9; 600/508; 600/515
(58) Field of Search ............................. 607/4, 5, 9, 14; 600/508, 509, 515–518

(56) References Cited

U.S. PATENT DOCUMENTS

| | | | |
|---|---|---|---|
| 5,291,400 A | 3/1994 | Gilham | 364/413.06 |
| 5,466,245 A | 11/1995 | Spinelli et al. | 607/17 |
| 5,560,370 A | 10/1996 | Verrier et al. | 128/705 |
| 5,603,331 A | 2/1997 | Heemels et al. | 128/696 |
| 5,645,570 A | 7/1997 | Corbucci | 607/5 |
| 5,682,901 A | 11/1997 | Kamen | 128/706 |
| 5,755,671 A | 5/1998 | Albrecht et al. | 600/516 |
| 5,842,997 A | * 12/1998 | Verrier et al. | 600/518 |
| 5,891,044 A | 4/1999 | Golosarsky et al. | 600/509 |
| 5,893,882 A | 4/1999 | Peterson et al. | 607/14 |
| 5,921,940 A | 7/1999 | Verrier et al. | 600/518 |
| 5,941,831 A | 8/1999 | Turcott | 600/515 |
| 6,021,351 A | 2/2000 | Kadhiresan et al. | 607/19 |
| 6,026,320 A | 2/2000 | Carlson et al. | 600/510 |

(List continued on next page.)

FOREIGN PATENT DOCUMENTS

| | | | |
|---|---|---|---|
| EP | 0709112 | 5/1996 | A61N/1/365 |
| WO | WO-94/06350 | 3/1994 | A61B/5/0452 |
| WO | WO-98/15319 | 4/1998 | A61N/1/365 |
| WO | WO-00/04950 | 2/2000 | A61N/1/368 |
| WO | WO-00/38782 | 7/2000 | A61N/1/368 |
| WO | WO-00/44274 | 8/2000 | |
| WO | WO 00/51680 | * 9/2000 | |
| WO | WO-00/51680 | 9/2000 | A61N/1/37 |

OTHER PUBLICATIONS

"Heart Rate Variability: Standards of Measurement, Physiological Interpretation, and Clinical Use", *Circulation, 93*, pp. 1043–1065, (1996).

Behrens, S., et al., "Effects of Amiodarone on the Circadian Pattern of Sudden Cardiac Death (Department of Vererans Affairs Congestive Heart Failure–Survival Trial of Antiarrhythmic Therapy)", *Am. J. Cardiol., 80*, pp. 45–48, (Jul. 1997).

(List continued on next page.)

*Primary Examiner*—George R. Evanisko
(74) *Attorney, Agent, or Firm*—Schwegman, Lundberg, Woessner & Kluth, P.A.

(57) ABSTRACT

A cardiac rhythm management system acquires atrial heart rate variability data. The system provides a graphic or other indication of patient well-being based on the atrial heart rate variability data. Such atrial heart rate variability information provides an indication of the autonomic balance between the sympathetic and parasympathetic/vagal components of the autonomic nervous system. One example of the system also provides time-domain processing of frequency components of the atrial heart rate interval signal to obtain the indication of patient well-being.

10 Claims, 11 Drawing Sheets

U.S. PATENT DOCUMENTS

| | | | | |
|---|---|---|---|---|
| 6,035,233 | A | * | 3/2000 | Schroeppel et al. ......... 600/515 |
| 6,042,548 | A | | 3/2000 | Giuffre ......................... 600/483 |
| 6,135,970 | A | | 10/2000 | Kadhiresan et al. ......... 600/595 |
| 6,144,878 | A | | 11/2000 | Schroeppel et al. ......... 600/515 |
| 6,216,032 | B1 | | 4/2001 | Griffin et al. ................ 600/515 |
| 6,224,553 | B1 | | 5/2001 | Nevo .......................... 600/437 |
| 6,246,909 | B1 | | 6/2001 | Ekwall ........................... 607/9 |
| 6,269,263 | B1 | | 7/2001 | Ohnishi et al. .............. 600/518 |
| 6,358,201 | B1 | | 3/2002 | Childre et al. .............. 600/300 |
| 6,390,986 | B1 | | 5/2002 | Curcie et al. ................ 600/485 |
| 6,480,733 | B1 | | 11/2002 | Turcott ........................ 600/516 |
| 2002/0029000 | A1 | | 3/2002 | Ohsaki |
| 2002/0072683 | A1 | | 6/2002 | Schroeppel et al. ......... 600/515 |

OTHER PUBLICATIONS

Behrens, S., et al., "Modification of the Circadian Pattern of Ventricular Tachyarrhythmias by Beta–Blocker Therapy", *Clin. Cardiol., 20,* pp. 253–257, (1997).

Berger, R.D., et al., "An Efficient Algorithm for Spectral Analysis of Heart Rate Variability", *IEEE Transactions on Biomedical Engineering, BME–33 (9),* pp. 900–904, (Sep. 1986).

Bigger, J.T., et al., "Correlations Among Time and Frequency Domain Measures of Heart Period Variability Two Weeks After Acute Myocardial Infarction", *Arrhythmias and Conduction Disturbances, 69,* pp. 891–898, (Apr. 1, 1992).

Bigger, Jr., J.T., "Spectral Analysis of R–R Variability to Evaluate Autonomic Physiology and Pharmacology and to Predict Cardiovascular Outcomes in Humans", *Am. J. Cardiol., 69,* pp. 891–898, (1992).

Bocker, D., et al., "Ventricular Resynchronization Therapy May Restore Autonomic Balance as Evidenced by Redicung the Low Frequency to High Frequency Autonomic Ratio in Heart Failure Patients", *4th International Meeting organized by the Working Group on Heart Failure of the European Society of Cardiology (Abstract),* Barcelona, Spain, 1 p., (Jun. 11, 2001).

Hayano, J., et al., "Circadian Rhythms of Atrioventricular Conduction Properties in Chronic Atrial Fibrillation With and Without Heart Failure", *JACC, 31 (1),* pp. 158–166, (Jan. 1998).

Lavery, C.E., et al., "Nonuniform Nighttime Distribution of Acute Cardiac Events", *Circulation, 96 (10),* pp. 3321–3327, (Nov. 18, 1997).

Peckova, M., et al., "Circadian Variations in the Occurence of Cardiac Arrests", *Circulation, 98 (1),* pp. 31–39, (1998).

Yamashita, T., et al., "Circadian Variation of Paroxysmal Atrial Fibrillation", *Circulation, 96 (5),* pp. 1537–1541, (Sep. 2, 1997).

"Heart Rate Variability: Standards of Measurement, Physiological Interpretation, and Clinical Use", *European Heart Journal, 17,* Prepared by the Task Force of The European Society of Cardiology and The North American Society of Pacing and Electrophysiology; published by the American Heart Association, Inc.; European Society of Cardiology, (1996),pp. 354–381.

Crawford, Michael.H. ,et al. ,"ACC/AHA Guidelines for Ambulatory Electrocardiography", *JACC,* vol. 34, No. 3, Published by Elsevier Science Inc., (Sep. 1999),912–948.

* cited by examiner

ATRIAL INTERVAL BASED HEART RATE VARIABILITY DIAGNOSTIC FOR CARDIAC RHYTHM MANAGEMENT SYSTEM

CROSS-REFERENCE TO RELATED APPLICATIONS

This patent application is a continuation-in-part of Gerrard M. Carlson et al. U.S. patent application Ser. No. 09/802,316, now U.S. Pat. No. 6,678,547 entitled "Cardiac Rhythm Management System Using Time-Domain Heart Rate Variability Indicia," filed on Mar. 8, 2001, and assigned to Cardiac Pacemakers, Inc., which is incorporated herein by reference in its entirety. This patent application is also related to Gerrard M. Carlson et al. U.S. patent application Ser. No. 09/704,844, entitled "LV Ectopic Density Trending," filed on Nov. 2, 2000, and assigned to Cardiac Pacemakers, Inc., which is incorporated herein by reference in its entirety.

TECHNICAL FIELD

The present system relates generally to cardiac rhythm management systems and particularly, but not by way of limitation, to such a system providing a diagnostic based at least in part on the variability of intervals between atrial heart contractions.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers coordinate atrial and ventricular contractions to improve pumping efficiency.

Cardiac rhythm management systems also include defibrillators that are capable of delivering higher energy electrical stimuli to the heart. Such defibrillators also include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. Other cardiac rhythm management systems combine the functions of pacers and defibrillators.

One problem faced by physicians treating cardiovascular patients is assessing patient well-being, either for providing a prognosis or for adjusting a therapy to improve the patient's prognosis. Ventricular heart rate variability ("HRV") is thought to provide one such assessment of cardiovascular health. The time interval between intrinsic ventricular heart contractions changes in response to the body's metabolic need for a change in heart rate and the amount of blood pumped through the circulatory system. For example, during a period of exercise or other activity, a person's intrinsic ventricular heart rate will generally increase over a time period of several or many heartbeats. However, even on a beat-to-beat basis, that is, from one heart beat to the next, and without exercise, the time interval between intrinsic heart ventricular contractions varies in a normal person. These beat-to-beat variations in intrinsic ventricular heart rate are the result of proper regulation by the autonomic nervous system of blood pressure and cardiac output; the absence of such variations indicates a possible deficiency in the regulation being provided by the autonomic nervous system.

The autonomic nervous system itself has two components: sympathetic and parasympathetic (or vagal). The sympathetic component of the autonomic nervous system is relatively slow acting, and is associated with a tendency to raise heart rate, blood pressure, and/or cardiac output. The parasympathetic/vagal component of the autonomic nervous system, which provides a relatively faster response than the sympathetic component, is associated with a tendency to reduce heart rate, blood pressure, and/or cardiac output. A proper balance between the sympathetic and parasympathetic components of the autonomic nervous system is important. Therefore, an indication of this balance of the components of the autonomic nervous system, which is sometimes referred to as "autonomic balance," "sympathetic tone," or "sympathovagal balance," provides a useful indication of the patient's well-being.

One technique for providing an indication of the balance of the components of the autonomic nervous system is provided by the beat-to-beat heart rate variability, as discussed above. More particularly, intrinsic ventricular contractions are detected. The time intervals between these contractions, referred to as the R-R intervals, are recorded after filtering out any ectopic contractions, that is, ventricular contractions that are not the result of a normal sinus rhythm. This signal of R-R intervals is typically transformed into the frequency-domain, such as by using fast Fourier transform ("FFT") techniques, so that its spectral frequency components can be analyzed. Two frequency bands are of particular interest: a low frequency (LF) band in the frequency ("f") range $0.04 \text{ Hz} \leq f \leq 0.15 \text{ Hz}$, and a high frequency (HF) band in the frequency range $0.15 \text{ Hz} \leq f \leq 0.40 \text{ Hz}$. The HF band of the R-R interval signal is influenced only by the parasympathetic/vagal component of the autonomic nervous system. The LF band of the R-R interval signal is influenced by both the sympathetic and parasympathetic components of the autonomic nervous system. Consequently, the ratio LF/HF is regarded as a good indication of the autonomic balance between sympathetic and parasympathetic/vagal components of the autonomic nervous system. An increase in the LF/HF ratio indicates an increased predominance of the sympathetic component, and a decrease in the LF/HF ratio indicates an increased predominance of the parasympathetic component. For a particular heart rate, the LF/HF ratio is regarded as an indication of patient wellness, with a lower LF/HF ratio indicating a more positive state of cardiovascular health.

The present inventors have recognized that such diagnostic techniques based on ventricular heart rate variability have certain limitations. For example, cardiac rhythm management systems typically include operational modes that do not track atrial heart rate. In such systems, ventricular heart rate variability is not necessarily representative of sinus rhythm and, therefore, is not necessarily representative of the balance between sympathetic and parasympathetic components of the autonomic nervous system. Moreover, even when the cardiac rhythm management system is operating in a mode that tracks atrial heart rate, R-R intervals that are associated with premature ventricular contractions (PVCs) must typically be ignored in any determination of sympathetic/parasympathetic balance based on ventricular heart rate variability. This reduces the amount of available data upon which the determination of sympathetic/parasympathetic balance is based. Furthermore, cardiac rhythm management systems may also include ventricular rate smoothing or ventricular rate stabilization algorithms. Because such techniques intentionally reduce or eliminate ventricular heart rate variability, they further confound any determination of sympathetic/parasympathetic balance based on ventricular heart rate variability. For these and other reasons, the present inventors have recognized that there is a need to provide improved diagnostic information indicative of sympathetic/parasympathetic balance.

SUMMARY

This document describes a cardiac rhythm management system that uses atrial heart rate variability to provide a diagnostic indication of patient well-being that reflects an autonomic balance between the sympathetic and vagal components of the autonomic nervous system. Such diagnostic information is available even when the cardiac rhythm management devices provides ventricular rate control therapy that does not track the atrial heart rate. Moreover, such atrial heart rate variability diagnostic information provides a more direct indication of sinoatrial rate, without being confounded by the presence of premature ventricular contractions (PVCs) or requiring techniques for minimizing the effects of PVCs. Furthermore, the atrial heart rate variability diagnostic information is available even when ventricular rate smoothing or stabilization algorithms are being used. The system, which includes both methods and apparatuses, provides graphical and other display techniques for presenting the atrial heart rate variability diagnostic information. In one embodiment, the system provides time-domain processing of atrial heart rate variability information to provide an indication of patient well-being based on the frequency content of an atrial heart rate interval signal. Other aspects of the invention will be apparent on reading the following detailed description, drawings, and claims.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

The present methods and apparatus are described and intended for use with respect to implantable cardiac rhythm management (CRM) devices, such as pacemakers, cardioverter/defibrillators, pacer/defibrillators, and multi-chamber and/or multi-site (in a single or multiple heart chambers) cardiac resynchronization therapy (CRT) devices. Such CRT devices are included within CRM devices even though the CRT devices need not necessarily modulate heart rate. Such CRT devices may instead provide contraction-evoking stimulations that establish or modify the conduction path of propagating depolarizations to obtain more efficient pumping of the heart. Moreover, the present methods and apparatus also finds application in other implantable medical devices, and in unimplanted (external) devices, including, but not limited to, external pacemakers, cardioverter/defibrillators, pacer/defibrillators, multi-chamber coordination devices, multi-site CRT devices, monitors, programmers and recorders, whether such devices are used for providing a diagnostic, a therapy, or both.

Figure 1:
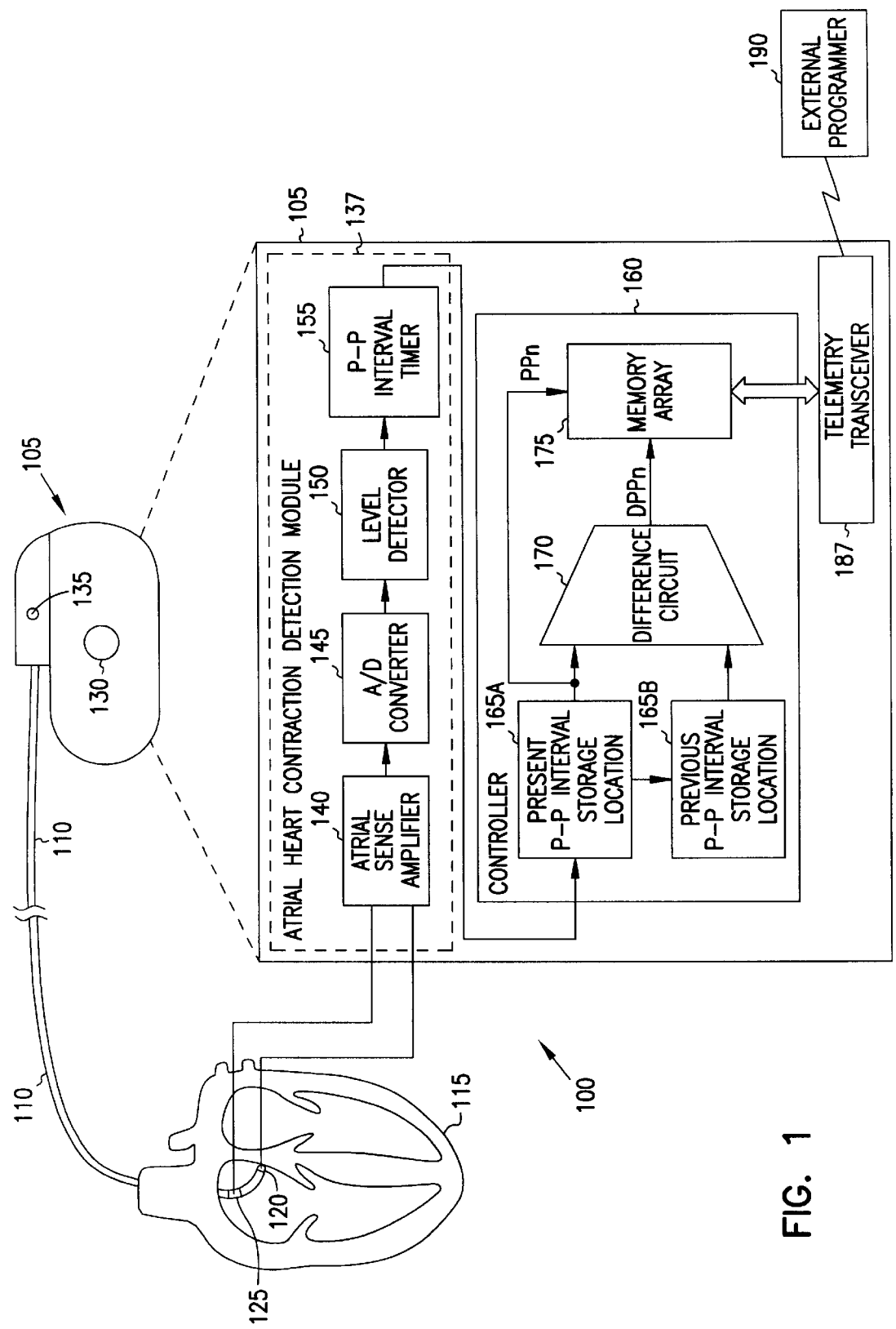
FIG. 1 is a schematic/block diagram of portions of a cardiac rhythm management system providing diagnostic information based at least in part on atrial heart rate variability.

FIG. 1 is a schematic/block diagram illustrating generally, by way of example, but not by way of limitation, one embodiment of portions of a cardiac rhythm management system 100. In this embodiment, system 100 includes, among other things, a cardiac rhythm management device 105 and a leadwire ("lead") 110 for communicating signals between device 105 and a atrial portion of heart 115. System 100 may also include additional components such as, for example, a remote programmer 190 capable of communicating with device 105 via a transmitter or receiver, such as telemetry transceiver 187.

In one embodiment, portions of system 100 (e.g., device 105) are implantable in a living organism, such as in a pectoral or abdominal region of a human patient, or elsewhere. In another embodiment, portions of system 100 (e.g., device 105) are alternatively disposed externally to the human patient. In the illustrated example, portions of lead 110 are disposed in the right atrium, however, any other positioning of lead 110 including atrially associated electrodes is included herein. For example, in various alternative embodiments, lead 110 may alternatively be positioned in a location that is associated with the superior vena cava, the coronary sinus or great cardiac vein, the left atrium, epicardially, or elsewhere. In one embodiment, lead 110 is a commercially available bipolar atrial pacing lead having a tip electrode 120 and a ring electrode 125 configured to be disposed in a right atrium of heart 115. In another embodiment, lead 110 includes electrodes associated with both atrial and ventricular chambers such as, for example, the right atrium and the right ventricle. System 100 can also include other leads and/or electrodes in addition to lead 110, appropriately disposed, such as in or around heart 115, or elsewhere. For example, in one external embodiment, device 105 is not implanted and lead 110 provides external surface ECG electrode connections for sensing atrial heart signals. In a unipolar example, implanted device 105 itself includes one or more atrial electrodes for sensing heart signals or providing therapy, such as housing electrode 130 or header electrode 135.

FIG. 1 also illustrates generally portions of device 105, together with schematic illustrations of example connections to the various electrodes. Device 105 includes an atrial heart contraction detection module 137 that receives intrinsic atrial heart signals from electrodes that are communicatively associated with a right or left atrium of heart 115. Module 137 provides an output heart rate interval signal carrying information about the time intervals between atrial heart contractions. Because the interval between atrial heart contractions manifests intrinsic variations in the sinus rhythm, the output atrial heart rate interval signal provided by module 137 includes atrial heart rate variability information.

In one example, module 137 includes an atrial sense amplifier 140. In the illustrated example, amplifier 140 is coupled to atrial tip electrode 120 and atrial ring electrode 125 for receiving intrinsic atrial heart signals. These atrial heart signals include electrical depolarizations corresponding to atrial heart contractions (right atrial heart contractions, in the illustrated example). Atrial sense amplifier 140 detects such input atrial heart depolarizations and provides an output electrical signal carrying such information to subsequent portions of device 105. In a further embodiment, atrial sense amplifier 140 also includes filtering or other signal processing circuits for detecting the desired electrical depolarizations associated with atrial heart contractions. Device 105 also includes an analog-to-digital (A/D) converter 145, which receives the sensed electrical depolarization signal and provides an output digital representation thereof. In a further embodiment, A/D converter 145 includes associated sample and hold circuits for sampling the electrical signal output by atrial sense amplifier 140. Peak or level detector 150 receives the digitized signal from A/D converter 145 and detects signal peaks or levels associated with atrial heart contractions. In this embodiment, these signal peaks or levels are the P-waves associated with atrial heart contractions.

In the illustrated embodiment, level detector 150 outputs information about the timing of each P-wave to P-P interval timer 155. Based on this information, P-P interval timer 155 outputs to controller 160 an indication of the duration of the time intervals between successive P-waves ("P-P intervals"). Controller 160 includes a storage location 165A, for storing the current P-P interval, $PP_n$ and another storage location 165B, for storing the immediately preceding P-P interval, $PP_{n-1}$. A difference circuit 170 receives $PP_n$ from storage location 165A and $PP_{n-1}$ from storage location 165B, and outputs a beat-to-beat difference, $DPP_n = PP_n - PP_{n-1}$, between successive P-P intervals. Controller 160 categorizes the P-P interval difference $DPP_n$ according to: (1) where $DPP_n$ falls within a range of such values, and (2) where $PP_n$ (or alternatively $PP_{n-1}$) falls within a range of such values. In one embodiment, memory array 175 is a two dimensional array indexed by (1) where $DPP_n$ falls within the range of such values, and (2) where $PP_n$ (or alternatively $PP_{n-1}$) falls within the range of such values. In one embodiment, the count in each memory location is initialized to zero at the beginning of a time period of interest (e.g., 24 hours), and incremented by one each time $DPP_n$ and $PP_n$ fall within the subranges corresponding to that particular memory location.

In one example, the displayed range of accumulated P-P intervals, PP, is approximately between 300 milliseconds and 1500 milliseconds inclusive, which is divided into X=32 subranges (also referred to as "bins"), and the displayed range of accumulated beat-to-beat differences, DPP, is approximately between 0 milliseconds and 120 milliseconds, which is divided into Y=16 bins. However, other ranges and/or number of bins of PP and DPP could also be used, moreover, such ranges and/or number of bins may also be based on previously acquired data so as to adjust the resolution of data being stored in memory array 175 to the actual data being acquired from a particular patient.

Figure 2:
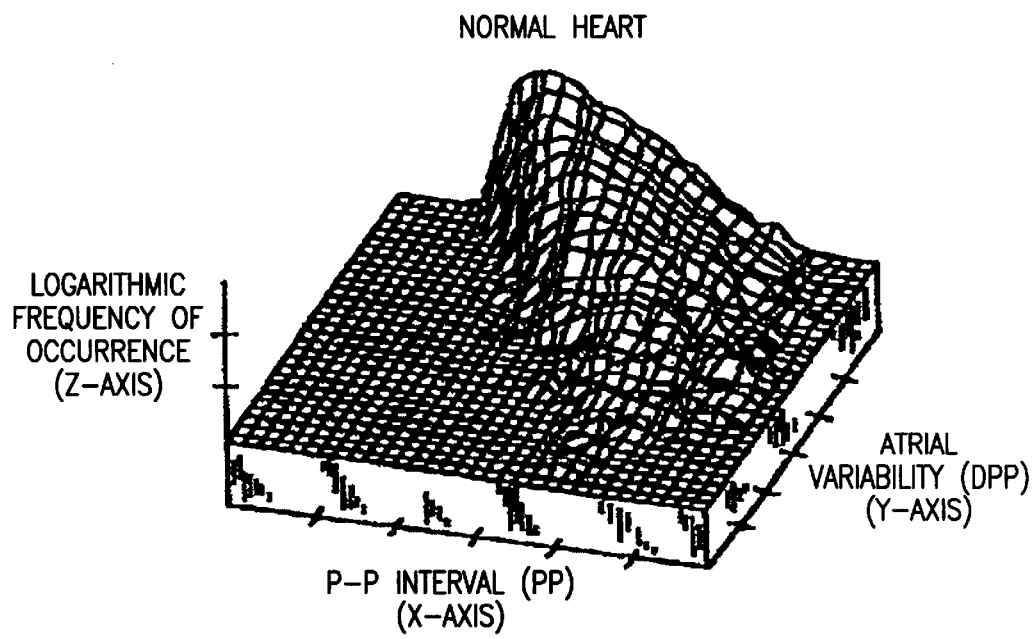
FIG. 2 is a graph displaying, for a normal heart, and a period of time, a frequency of occurrence of atrial contractions as a function of a P-P interval duration and a time difference between successive P-P intervals.
Figure 3:
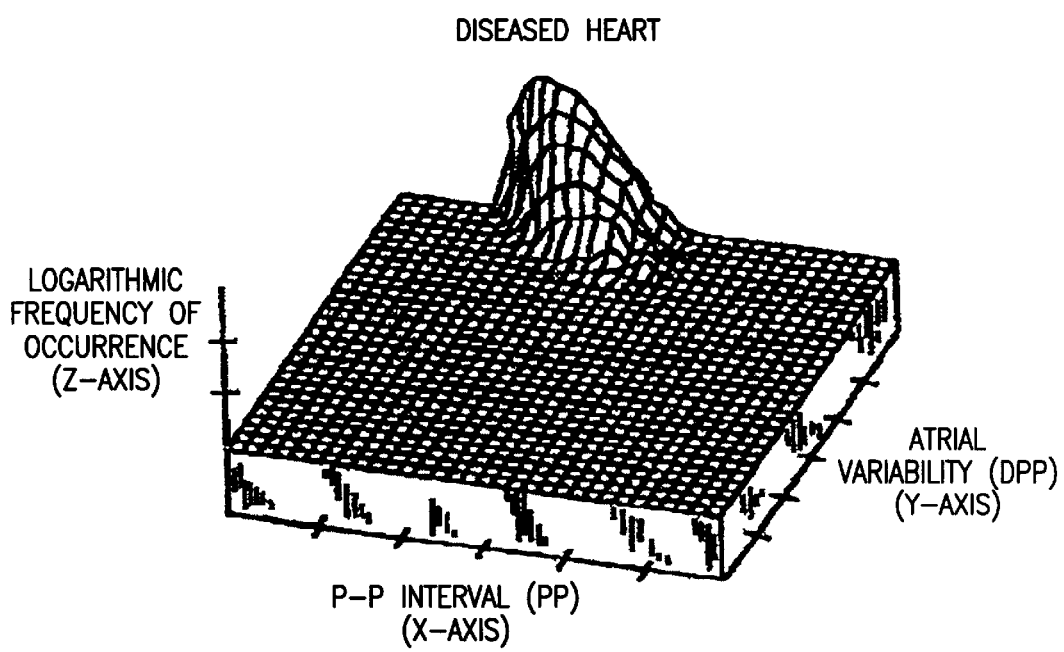
FIG. 3 is a graph displaying, for a diseased heart, and a period of time, a frequency of occurrence of atrial contractions as a function of the P-P interval duration and the time difference between successive P-P intervals.
Figure 4:
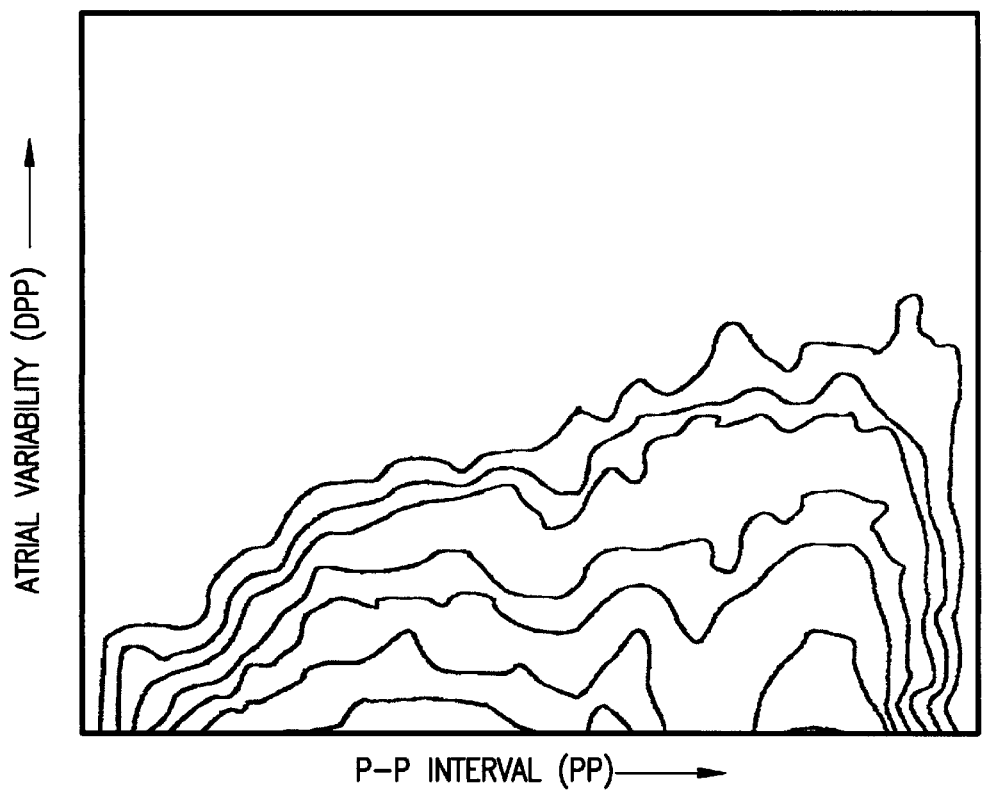
FIG. 4 is a graph using contour lines for displaying, for a period of time, a frequency of occurrence of atrial contractions as a function of the P-P interval duration and the time difference between successive P-P intervals.

In a further embodiment, after a period of time during which data is accumulated in memory array 175, transceiver 187 communicates the data in memory array 175 to external programmer 190 for display. FIGS. 2 and 3 are histograms illustrating generally one example of displaying such data. In this example, the stored counts are scaled logarithmically for display on a Z-axis against an X-axis, indicating P-P interval amount, and a Y-axis, indicating atrial heart rate variability. FIGS. 2 and 3 respectively illustrate expected distributions for a normal heart and a diseased heart. Because these expected distributions are different for different stages of disease progression, their display provides a useful diagnostic of patient well-being. FIG. 4 illustrates generally another example of displaying such data using contour lines to provide an indication of the frequency of occurrence of (PP, DPP) pairs. Details regarding the generation of such data displays is described in Heemels et al. U.S. Pat. No. 5,603,331 entitled "Data Logging System For Implantable Cardiac Device," assigned to Cardiac Pacemakers, Inc., the disclosure of which is incorporated by reference in its entirety.

In yet another example, programmer 190 provides a metric for quantifying the observed distribution of indexed counts. In one example, for a given pair of ranges over which the (PP, DPP) paired data is collected over a period of time, a "fractional-filled" metric indicates the percentage of locations in memory array 175 for which the stored count equals or exceeds zero or some other threshold value. Examples of other metrics include minimum, median, mean, and/or maximum observed PP, minimum, median, mean, and/or maximum observed DPP, and standard deviation or variance of the observed PP and/or DPP.

FIGS. 2–4 provide examples of two dimensional display of atrial heart rate variability data. Such displays are very useful to the physician in that a sick patient will typically show a higher heart rate (shorter PP) and lower heart rate variability (smaller DPP), in comparison to an improved patient, who will typically have a lower heart rate (longer PP) and increased heart rate variability (larger DPP). Moreover, because such diagnostic indicators are based on atrial heart rate variability data, rather than ventricular heart rate variability data, problems associated with using ventricular heart rate data are avoided. For example, the atrial heart rate variability data provides useful diagnostic information even when the cardiac rhythm management device is operating in a mode that does not track atrial heart rate. By contrast, in such modes, ventricular heart rate variability is not necessarily representative of sinus rhythm and, therefore, is not necessarily representative of the balance between sympathetic and parasympathetic components of the autonomic nervous system. Moreover, even when the cardiac rhythm management system is operating in a mode that tracks atrial heart rate, ventricular heart rate variability data requires that R-R intervals associated with premature ventricular contractions (PVCs) be ignored. This reduces the amount of available data upon which a diagnosis is based. By contrast, the present atrial heart rate variability diagnostic techniques can make use of data from all atrial heart contractions, which increases the available data for making the diagnosis, and reduces the complexity of making the diagnosis, since techniques for ignoring PVC's are not needed. The present atrial heart rate variability diagnostic techniques are also well-suited for cardiac rhythm management systems using ventricular rate smoothing or ventricular rate stabilization algorithms. Because such techniques intentionally reduce or eliminate ventricular heart rate variability, they further confound any determination of sympathetic/parasympathetic balance based on ventricular heart rate variability. In such circumstances, however, the present atrial heart rate variability techniques are still capable of providing useful diagnostic information.

Figure 5:
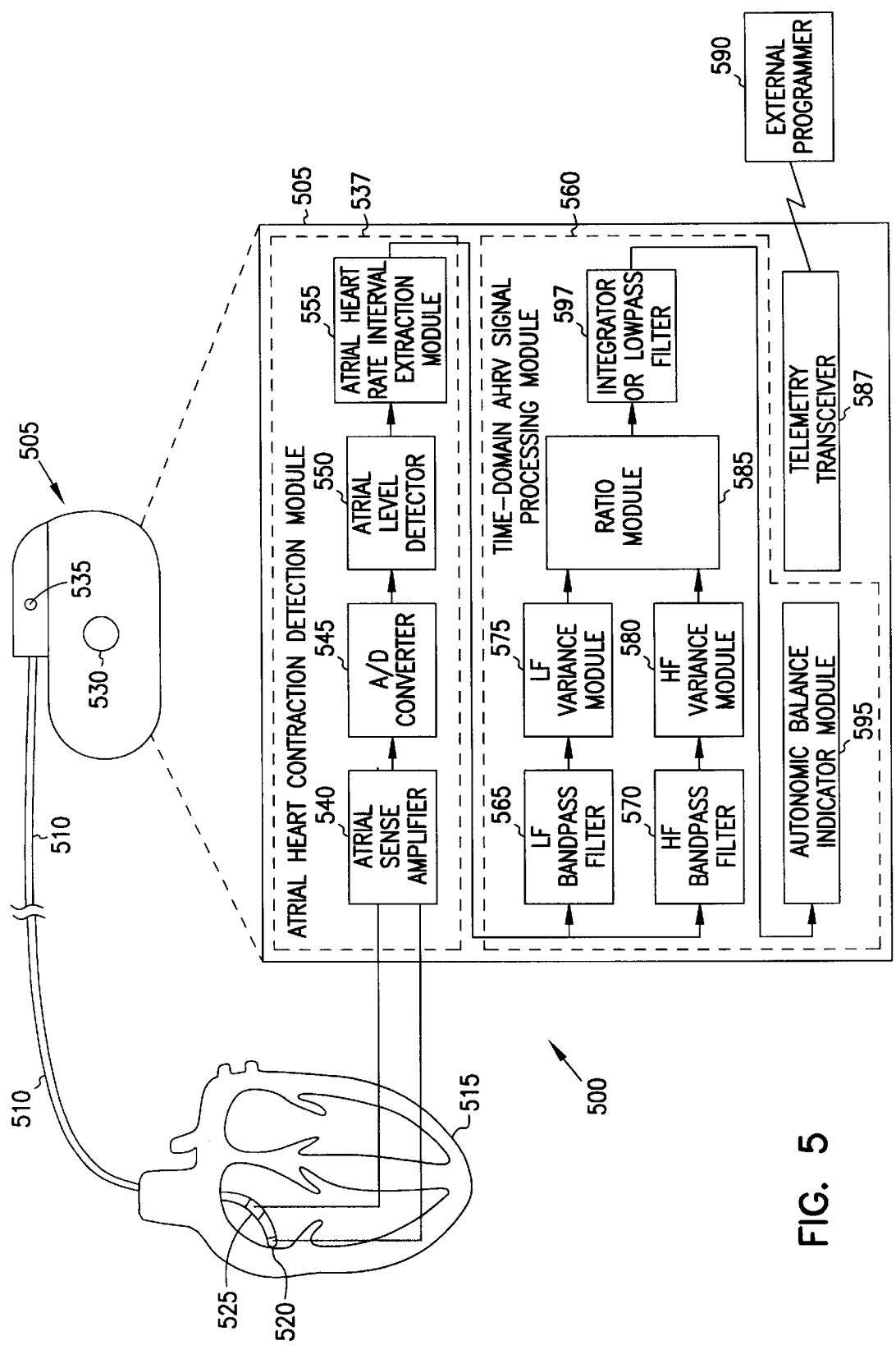
FIG. 5 is a schematic/block diagram of portions of a cardiac rhythm management system providing time-domain processing of atrial heart rate interval information to provide diagnostic information.

FIGS. 5–12 illustrate another example of providing a diagnostic indication of patient wellness based on atrial heart rate variability, including time-domain signal processing of the atrial heart rate variability signal. FIG. 5 is a schematic/block diagram illustrating generally one example of portions of a cardiac rhythm management system 500. In this embodiment, system 500 includes, among other things, a cardiac rhythm management device 505 and a leadwire ("lead") 510 for communicating signals between device 505 and a portion of a living organism, such as a heart 515. System 500 may also include additional components such as, for example, a remote programmer 590 capable of communicating with device 505 via a transmitter or receiver, such as telemetry transceiver 587.

In one embodiment, portions of system 500 (e.g., device 505) are implantable in the living organism, such as in a pectoral or abdominal region of a human patient, or elsewhere. In another embodiment, portions of system 500 (e.g., device 505) are alternatively disposed externally to the human patient. In the illustrated embodiment, portions of lead 510 are disposed in the right atrium and/or superior vena cava, however, such portions of lead 510 could alternatively be disposed in portions of the coronary sinus or left atrium, or epicardially associated with any of these regions. In one embodiment, lead 510 is a commercially available bipolar pacing lead having a tip electrode 520 and a ring electrode 525 configured to be disposed in a right atrium of heart 515. System 500 can also include other leads and/or electrodes in addition to lead 510, appropriately disposed, such as in or around heart 515, or elsewhere. For example, in one external embodiment, device 505 is not implanted and lead 510 provides external surface ECG electrode connections for sensing atrial heart signals. In a unipolar example, implanted device 505 itself includes one or more electrodes for sensing heart signals or providing therapy, such as housing electrode 530 or header electrode 535.

FIG. 5 also illustrates generally portions of device 505, together with schematic illustrations of example connections to the various electrodes. Device 505 includes an atrial heart contraction detection module 537 that receives intrinsic atrial heart signals from electrodes that are communicatively associated with an atrial portion of heart 515. Module 537 provides an output atrial heart rate interval signal carrying information about the time intervals between atrial heart contractions. Because, the interval between atrial heart contractions manifests intrinsic sinoatrial variations influenced by the sympathetic and parasympathetic branches of the nervous system, the output atrial heart rate interval signal provided by module 537 includes atrial heart rate variability information.

In one embodiment, module 537 includes an atrial sense amplifier 540, which, in this illustration, is coupled to tip electrode 520 and ring electrode 525 for receiving intrinsic atrial heart signals that include electrical depolarizations corresponding to atrial heart contractions (right atrial heart contractions, in this example). Sense amplifier 540 detects such input atrial heart depolarizations and provides an output electrical signal carrying such information to subsequent portions of device 505. In a further embodiment, sense amplifier 540 also includes filtering or other signal processing circuits for detecting the desired electrical atrial depolarizations associated with heart contractions. Device 505 also includes an analog-to-digital (A/D) converter 545, which receives the sensed electrical atrial depolarization signal and provides an output digital representation thereof. In a further embodiment, A/D converter 545 includes associated sample and hold circuits for sampling the electrical atrial heart signal output by sense amplifier 540. Atrial peak or level detector 550 receives the digitized signal from A/D converter 545 and detects signal peaks or levels associated with atrial heart contractions. In this embodiment, these signal peaks or levels are the P-waves associated with atrial depolarizations.

In the illustrated embodiment, peak or level detector 550 outputs information about the timing of each P-wave to atrial heart interval extraction module 555. Based on this information, atrial heart rate interval extraction module 555 provides a discrete-time signal that is periodically sampled, i.e., the time difference between such samples is uniform. Each such sample includes an associated time interval ("atrial heart rate interval") corresponding to the detected atrial heart rate.

Figure 6:
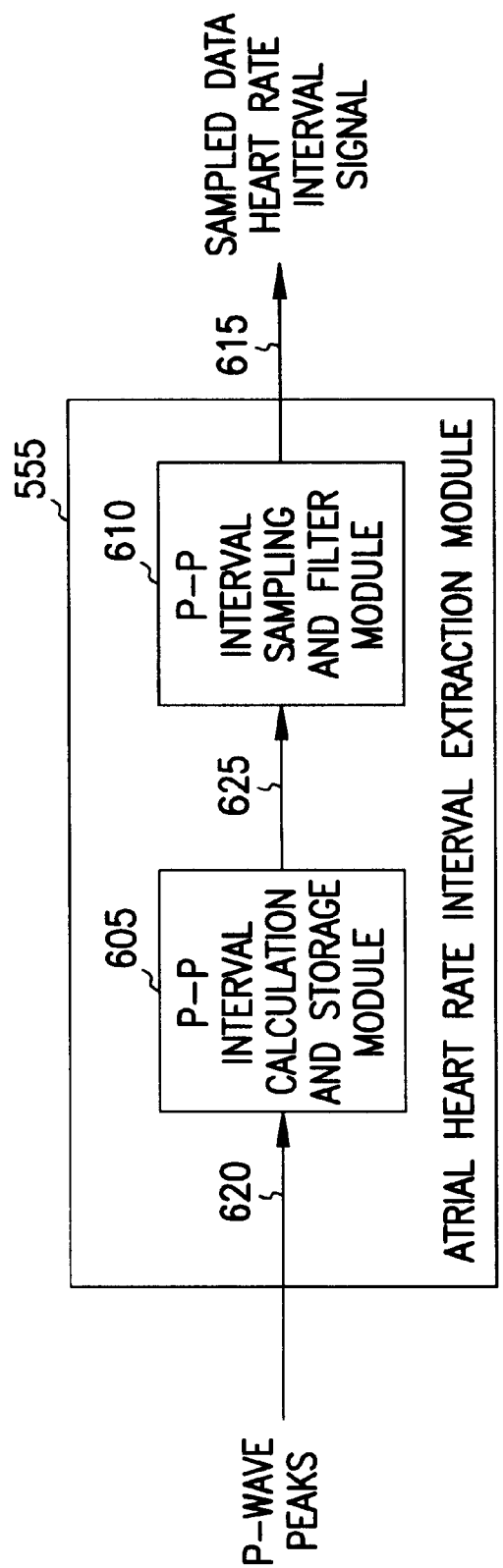
FIG. 6 is a block diagram of portions of an atrial heart rate interval extraction module.

FIG. 6 is a schematic/block diagram, illustrating generally one example of portions of atrial heart rate interval extraction module 555, which includes a P-P interval calculation and storage module 605, and a P-P interval sampling and filter module 610. Atrial heart rate interval extraction module 555 outputs a sampled data atrial heart rate interval signal 615 that includes P-P interval information. In FIG. 6, module 605 receives the detected P-waves from peak or level detector 550.

Figure 7:
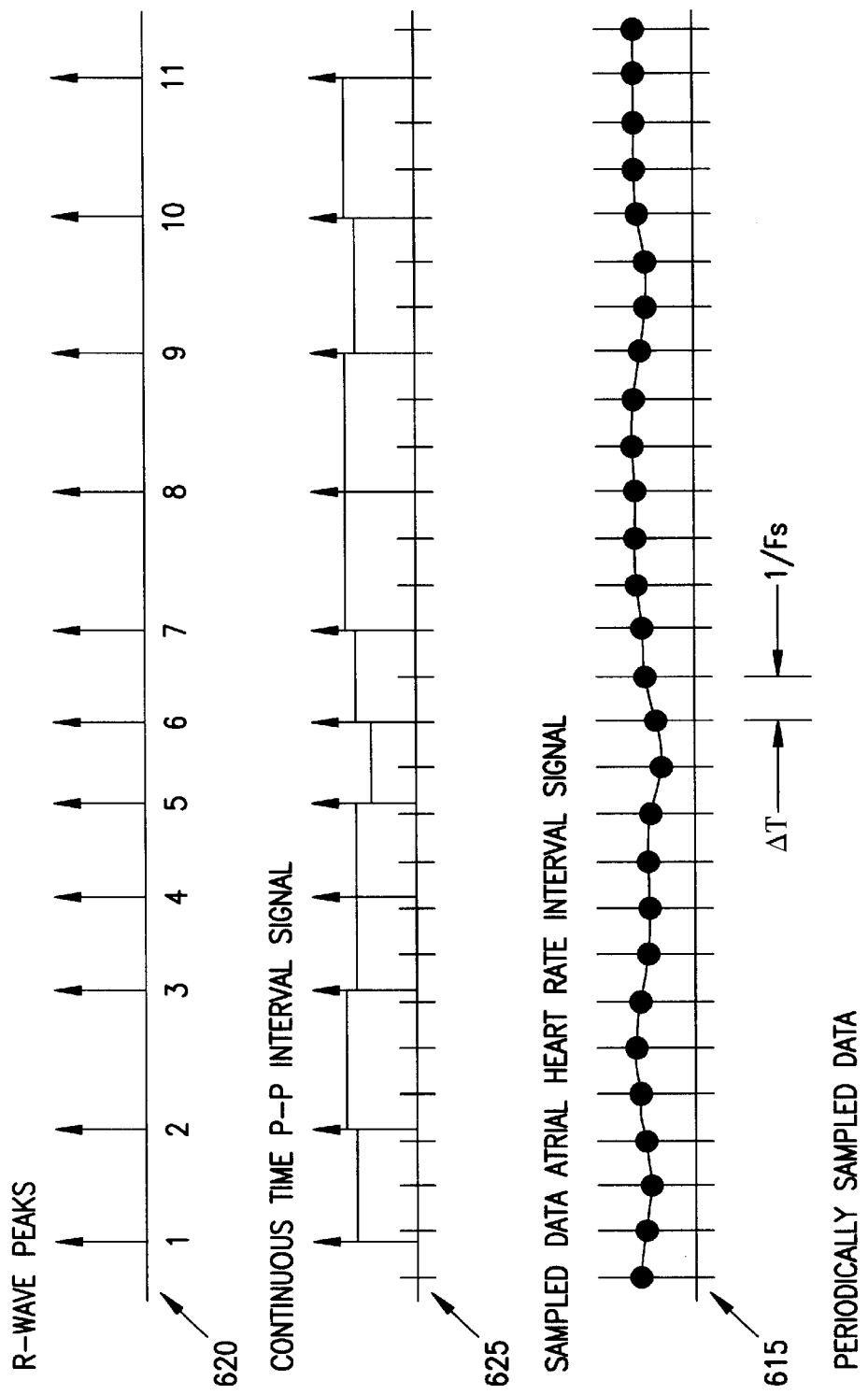
FIG. 7 is a graph illustrating one technique for obtaining a sampled data atrial heart rate interval signal from a sequence of detected P-wave peaks.
Figure 8:
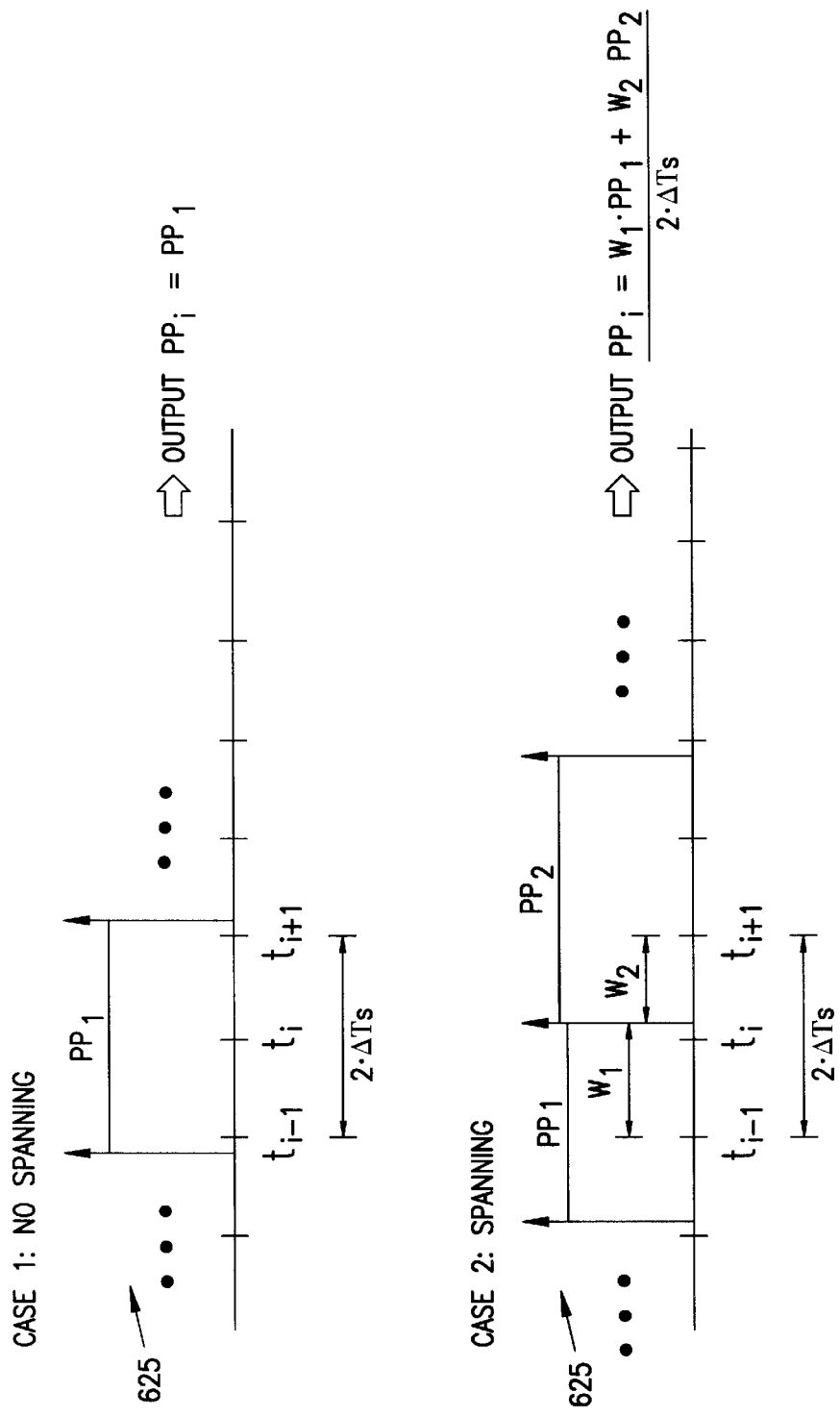
FIG. 8 is a graph further illustrating one technique for obtaining a sampled data atrial heart rate interval signal from a continuous time P-P interval signal.

FIG. 7 is a signal graph illustrating generally one example of the operation of P-P interval calculation and storage module 605 and P-P interval sampling and filter module 610. P-P interval calculation and storage module 605 receives a signal at node 620 including P-waves. Module 605 includes a timer that determines the PP time interval between detected P-waves, and stores the P-P intervals in memory to provide a resulting continuous time P-P interval signal at node 625. The signal at node 625 is sampled by module 610 to produce the resulting sampled data atrial heart rate interval signal at node 615, which includes P-P interval information.

In one embodiment, module 610 includes a sampling module that samples the signal at node 625 at a sampling frequency, $f_S$, exceeding the Nyquist criterion. For example, if the maximum expected atrial heart rate is 180 beats per minute, then a sampling rate that is greater than or equal to 6 Hz is sufficient. In one embodiment, this sampling module portion of module 610 also includes a finite impulse response (FIR) lowpass filter (or similar lowpass filter, averager, decimator, or downsampler) that provides a smoothed sampled data heart rate interval signal 610.

In one embodiment, a three sample point FIR filter is used to sample and filter the continuous time P-P interval signal at node 625. These sample points are separated from each by a time interval, $\Delta T_S$, where $\Delta T_S$ is the inverse of the sampling frequency, $f_S$. In operation, if the three sample points (at times $t=t_{i-1}, t_i, t_{i+1}$) fall within the same P-P interval of the continuous time P-P interval signal at node 625, then that P-P interval value is used as the corresponding output sample, $PP_i$. Otherwise, if the three sample points span a pair of P-P intervals (i.e., first and second P-P intervals, $PP_1$ and $PP_2$) on the continuous time P-P interval signal at node 625, a weighted average of the first and second P-P interval values is used as the corresponding output sample, $PP_i$. Each of the first and second P-P interval values is weighted according to the fraction of the time, $(t_{i+1}-t_{i-1})$ associated with that one of the first and second P-P intervals, $PP_1$ and $PP_2$. An example of operating such a filter is illustrated generally by FIG. 8.

FIG. 5 also illustrates a time-domain atrial heart rate variability (AHRV) signal processing module 560 that receives the atrial heart rate interval signal at node 615 from atrial heart rate interval extraction module 555, and provides a resulting indicator of patient well-being. In one embodiment of AHRV signal processing module 560, the input atrial heart rate interval signal at node 615 is received by a low frequency (LF) bandpass filter 565 and by a high frequency (HF) bandpass filter 570. In one embodiment, LF bandpass filter 565 is a finite impulse response (FIR) type filter having a lowpass cutoff frequency that is approximately equal to 0.15 Hz, and a highpass cutoff frequency that is approximately equal to 0.04 Hz. As a result, LF bandpass filter 565 outputs a filtered atrial heart rate interval signal having frequency components that are primarily approximately between 0.04 Hz and 0.15 Hz inclusive. In this embodiment, HF bandpass filter 570 is an FIR type filter having a lowpass cutoff frequency that is approximately equal to 0.40 Hz, and a highpass cutoff frequency that is approximately equal to 0.15 Hz. As a result, HF bandpass filter 570 outputs a filtered atrial heart rate interval signal having frequency components approximately between 0.15 Hz and 0.40 Hz inclusive. Appropriate infinite impulse response (IIR) filter structures could also be used. Since the ultimate measurement of patient well-being is based on variance, waveform distortion is not of great concern and, therefore, the filter need not provide linear phase.

LF variance module 575 and HF variance module 580 receive the output signals from LF bandpass filter 565 and HF bandpass filter 570, respectively. These variance modules 575 and 580 each perform a variance-type or similar computation, respectively outputting LF variance and HF variance signals to ratio module 585. In one embodiment, variance modules 575 and 580 each include a squaring circuit (i.e., a circuit that multiplies the input by itself to provide an output signal that is equivalent to the input signal raised to the second power) followed by a lowpass filter (or integrator or averager) to provide the resulting output signal. This squaring and lowpass filtering operation is equivalent to a variance computation that provides an indication of atrial heart rate variability within the associated frequency range. In one embodiment, the lowpass filter used by variance modules 575 and 580 is an IIR type filter having a single lowpass pole with exponential weighting of past samples occurring during a moving time window that is approximately between 2 and 5 minutes, inclusive, in length.

Ratio module 585 receives the LF and HF variance output signals from LF variance module 575 and HF variance module 580, respectively, and divides the value of the LF variance by the HF variance. The resulting LF/HF ratio output by ratio module 585 provides an indication, based on atrial heart rate variability, of the sympathovagal balance between the sympathetic and parasympathetic/vagal components of the autonomic nervous system. An increase in the LF/HF ratio indicates an increased predominance of the sympathetic component, and a decrease in the LF/HF ratio indicates an increased predominance of the parasympathetic component. For a particular atrial heart rate, the LF/HF ratio is regarded as an indication of patient wellness, with a lower LF/HF ratio indicating a more positive state of cardiovascular health. In one embodiment, this LF/HF ratio output by ratio module 585 is itself used as a patient wellness indicator. In further embodiments, however, this LF/HF ratio signal undergoes further processing, as discussed below.

For example, in one such further embodiment, the LF/HF ratio signal output by ratio module 585 is received by a lowpass filter (or integrator or averager) 597 to provide additional smoothing of the indication of patient well-being. In one such example, lowpass filter 597 is implemented as an exponential-weighted averager (i.e., more recent samples are weighted more than older samples) over a sliding time window that is approximately between 2 minutes and 5 minutes inclusive, such as about 5 minutes. The resulting smoothed LF/HF ratio signal output by lowpass filter 597 provides a more stable indication of the patient's sympathovagal balance; one such smoothed LF/HF ratio signal is illustrated generally, by way of example, but not by way of limitation, in the graph of FIG. 9, together with a corresponding sample atrial heart rate interval signal on which the smoothed LF/HF ratio is based.

Figure 9:
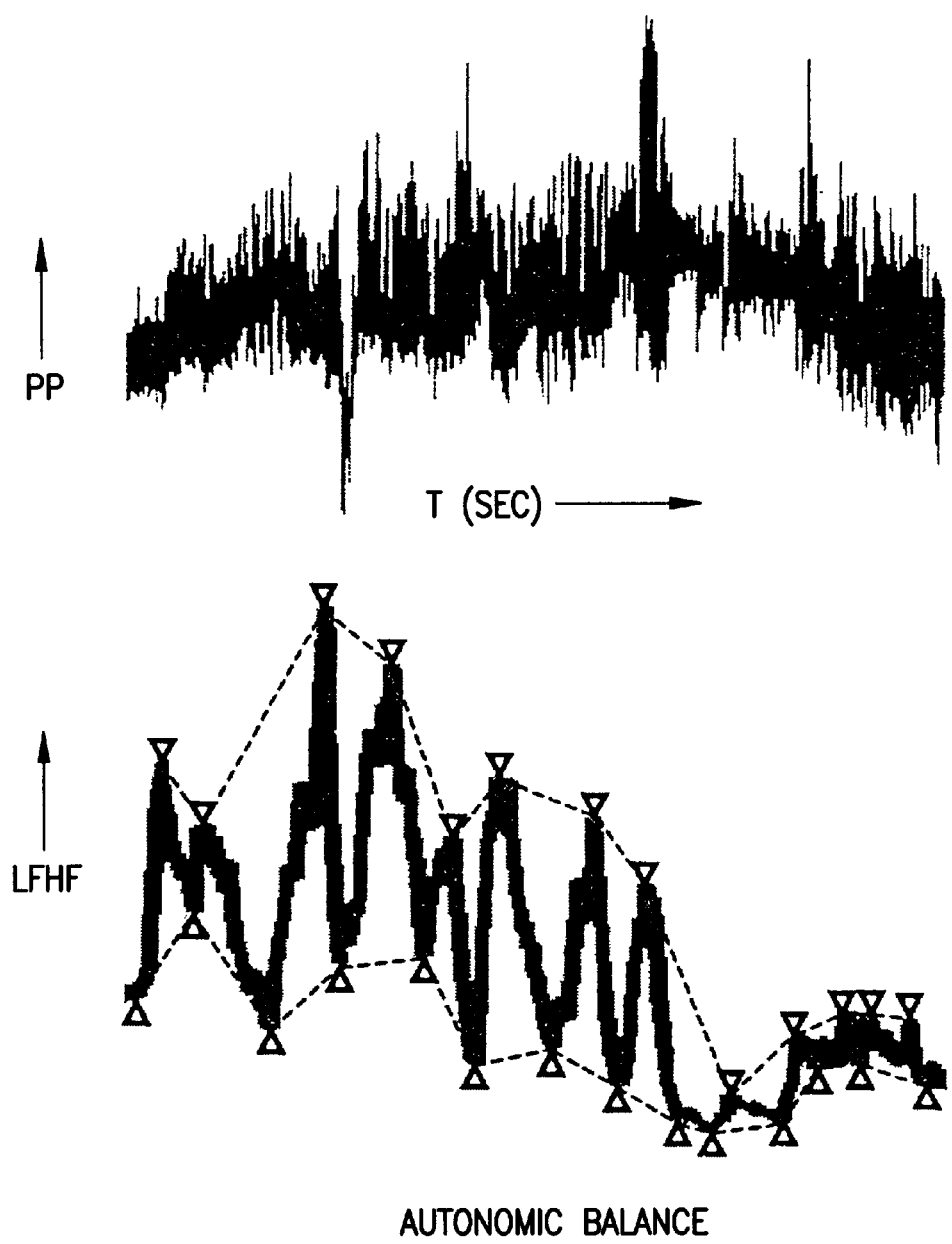
FIG. 9 is a graph illustrating one technique for providing a smoothed indicator of autonomic balance from P-P interval data.

In a still further embodiment, the smoothed LF/HF ratio signal is received by autonomic balance indicator module 595 for further processing. In one example, module 595 includes a peak detector for obtaining the local minima and/or maxima of the smoothed LF/HF ratio signal, as illustrated in FIG. 9. Thus, in one embodiment, the indication of autonomic balance is based on one or more features of the smoothed LF/HF ratio signal, such as the local minima (e.g., using the lowest local minima during a given time period, an average of the local minima during a given time period, etc.), the local maxima, slope of the smoothed LF/HF ratio signal, and/or slope of portions of the LF/HF envelope (e.g., lines drawn between successive local minima and lines drawn between successive local maxima). In a further embodiment, the desired indication of autonomic balance is communicated by telemetry transceiver 587 to external programmer 590, such as for processing and/or for visual, audible, or other diagnostic display to the physician or other user.

Figure 10:
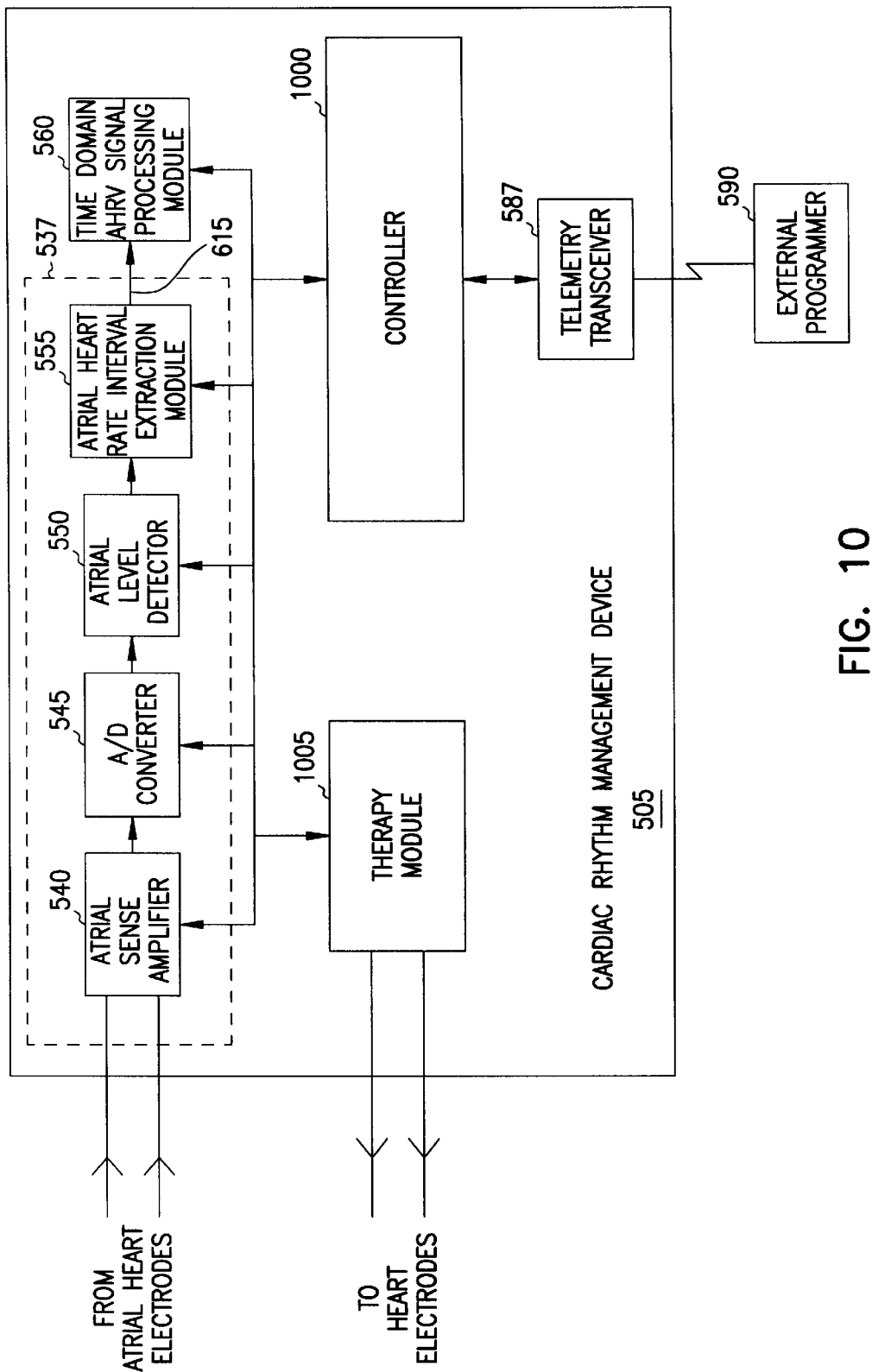
FIG. 10 a schematic/block diagram of portions of a cardiac rhythm management device that provides therapy to a heart based at least in part on information obtained from atrial heart rate variability.

FIG. 10 is a schematic/block diagram illustrating generally, by way of example, and not by way of limitation, one embodiment of portions of device 505 including a controller 1000 and a therapy module 1005. Therapy module 1005 provides cardiac rhythm management therapy to one or more atria or ventricles of heart 515 via electrodes that are communicatively associated therewith. Examples of such therapy include, without limitation, atrial or ventricular pacing therapy, atrial or ventricular antitachyarrhythmia therapy, atrial or ventricular multi-site coordination therapy, such as biventricular pacing or univentricular multi-site pacing, and/or drug delivery. In one such embodiment, the parameters of such therapy are adjusted and/or optimized by controller 1000 based at least in part on one or more indications of sympathetic/parasympathetic balance obtained from time-domain AHRV signal processing module 560. For example, such parameters for providing dual chamber pacing therapy are well known in the art (e.g., rate, amplitude, pulse width, AV-delay, etc.); such parameters are adjusted, either individually or in combination, to increase or decrease a particular indication of autonomic balance (e.g., to decrease the lowest local minima of the smoothed LF/HF signal). Such parameter optimization is performed either in device 505 or, alternatively, in external programmer 590.

In another example, the real-time (i.e., not substantially delayed) indicator of sympathetic/vagal balance provided by module 560 alerts the device to time periods during which heart 515 is particularly susceptible to tachyarrhythmias, such as when the smoothed or unsmoothed LF/HF signal increases (e.g., beyond a threshold value or at a rate that exceeds a threshold rate). In this embodiment, the increase in the LF/HF indication predicts the likely present or future onset of a tachyarrhythmia and, as a result, controller 1000 triggers the delivery of preventative antitachyarrhythmia therapy to prevent the occurrence of the tachyarrhythmias. Such antitachyarrhythmia therapy includes antitachyarrhythmia pacing (ATP) sequences and/or antiarrhythmic drug therapy using drugs that increase parasympathetic and/or decrease sympathetic activity. Thus, this embodiment provides real-time control of therapy delivery based on the then-existing (or slightly delayed) indication of sympathetic/vagal balance, as derived from atrial heart rate variability.

Figure 11:
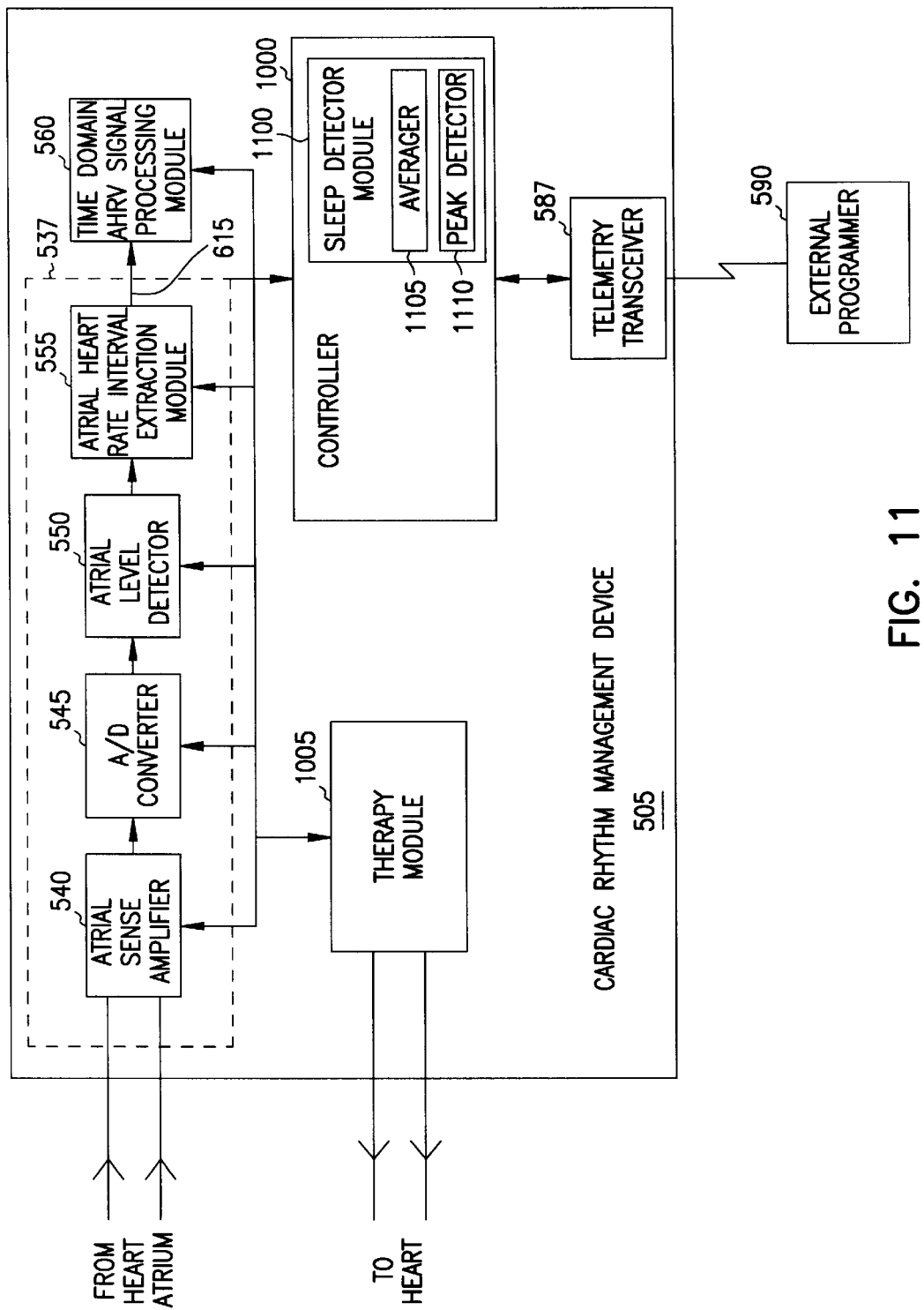
FIG. 11 is a schematic/block diagram of portions of a cardiac rhythm management device that includes a sleep detector for establishing a time period for acquiring atrial heart rate variability data.
Figure 12:
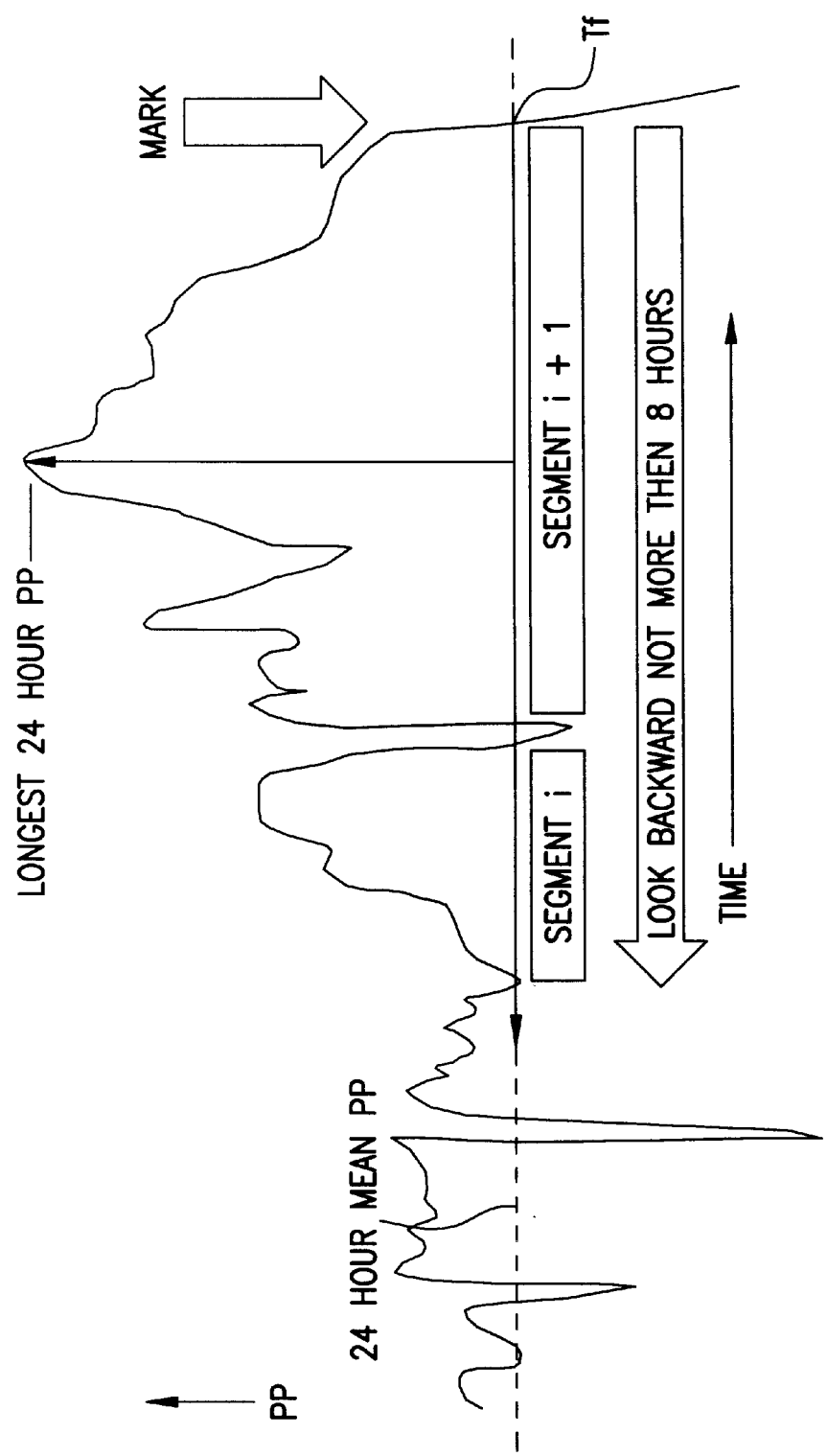
FIG. 12 is a graph illustrating one technique of operating a sleep detector for acquiring atrial heart rate variability data.

FIG. 11 is a schematic/block diagram illustrating generally, by way of example, but not by way of limitation one embodiment of portions of device 505 in which controller 1000 (or, alternatively, external programmer 590) includes a "sleep detector" module 1100 or other similar module for identifying one or more particular time periods of interest for obtaining the indication of sympathetic/vagal balance. In one embodiment, sleep detector 1100 includes a long term (e.g., 24 hour) averager 1105 for storing the long term average interval between atrial heart contractions (e.g., P-P interval), and a long term (e.g., 24 hour) peak detector 1110 for storing a corresponding long term maximum interval between atrial heart contractions (e.g., maximum P-P interval). In this embodiment, autonomic balance indicator module 595 of FIG. 5 provides an indication of patient well-being based on sympathetic/vagal balance as obtained only when the interval between atrial heart contractions exceeds the long term average value over a time period that: (1) extends forward in time from the time corresponding to the maximum interval between atrial heart contractions to the first time, $T_f$, at which the interval between atrial heart contractions drops back to the long term average value; and (2) extends backward in time from the time corresponding to the maximum interval between atrial heart contractions to a time that is not more than 8 hours (by way of example) earlier than the time $T_f$. Intervals during this time period in which the interval between atrial heart contractions is less than the long term average value are, in one embodiment, ignored for the purposes of providing an indication of sympathetic/parasympathetic balance. This described technique is illustrated generally, by way of example, but not by way of limitation, in FIG. 12. This technique is particularly useful for ascertaining longer term (e.g., over a period of days or months) variations in the patient's well-being as determined from sympathetic/parasympathetic balance. Because exercise, posture, and even being awake affect the sympathetic/parasympathetic balance, these factors are de-emphasized for ascertaining such longer term variations in the patient's well-being. While the time periods used in such techniques may be deemed "sleep," as referred to in this document by the use of the term "sleep detector module," it is understood that such times may not correspond exactly to periods during which the patient is sleeping. Other suitable time periods may also be used to de-emphasize components of the patient's sympathetic/vagal balance that tend to confound an assessment of long-term well-being.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A method including:
   detecting, over a time period, intrinsic atrial heart contractions;
   sampling P-P intervals between the intrinsic atrial heart contractions to obtain a time-domain P-P interval signal;
   filtering the P-P interval signal to obtain a time-domain second signal including frequency components substantially in a first frequency band, wherein the second signal is influenced by both sympathetic and parasympathetic components of the autonomic nervous system;

filtering the P-P interval signal to obtain a time-domain third signal including frequency components substantially in a second frequency band, wherein the third signal is influenced by the parasympathetic component of the autonomic nervous system and not substantially influenced by the sympathetic component of the autonomic nervous system;

determining a time domain variance of each of the second and third signals; and providing an indication associated with a balance between sympathetic and parasympathetic components of the autonomic nervous system based on the variances of the time-domain second and third signals.

2. The method of claim 1, in which providing the indication includes determining a ratio of the variances of the second and third signals.

3. The method of claim 1, further including disposing an atrial electrode in an atrium of a heart.

4. The method of claim 1, further including:

calculating at least one beat-to-beat P-P time difference between successive P-P time intervals; and adjusting a cardiac rhythm management therapy using the at least one P-P time difference.

5. The method of claim 1, wherein, when a ventricular rate smoothing or ventricular rate regulation is turned on to reduce variability in the ventricular heart rate, then using the detecting the intrinsic atrial heart contractions for the providing the indication of the balance between sympathetic and parasympathetic components of the autonomic nervous system.

6. A system including:

an atrial electrode configured for being associated with an atrium;

an atrial sense amplifier, including an atrial sense amplifier input coupled to the atrial electrode for receiving, over a time period, intrinsic atrial electrical depolarizations therefrom, and including an atrial sense amplifier output;

a P-P interval timer, including a P-P timer input coupled to the atrial sense amplifier output for receiving intrinsic atrial electrical depolarizations, and including an P-P timer output providing a P-P interval signal based on a P-P interval between successive atrial heart contractions;

a low frequency (LF) bandpass filter, coupled to the P-P timer output for receiving the P-P interval signal, the LF bandpass filter providing a time-domain LF signal output that is influenced by both the sympathetic and parasympathetic components of the autonomic nervous system;

a high frequency (HF) bandpass filter, coupled to the P-P timer output for receiving the P-P interval signal, the HF bandpass filter providing a time-domain HF signal output having higher frequency components than the LF signal output, the HF signal output being influenced by the parasympathetic component of the autonomic nervous system and not substantially influenced by the sympathetic component of the autonomic nervous system;

an LF variance module coupled to the LF bandpass filter for receiving the LF signal, the LF variance module providing a resulting LF variance signal;

a HF variance module, coupled to the HF bandpass filter for receiving the HF signal, the HF variance module providing a resulting HF variance signal; and an autonomic balance indicator module, coupled to the LF and HF variance modules, and providing an indication of a balance between sympathetic and parasympathetic components of an autonomic nervous system based on using the LF and HF variance signals.

7. The system of claim 6, in which the autonomic balance indicator module provides the indication of the balance between sympathetic and parasympathetic components of the autonomic nervous system based on a ratio of a low frequency component of the P-P interval signal to a high frequency component of the P-P interval signal.

8. The system of claim 6, further including a therapy module coupled to the autonomic balance indicator module, the therapy module to provide a cardiac rhythm management therapy based on using the indication of the balance.

9. The system of claim 8, wherein the autonomic balance indicator provides the balance indication using a ratio of the LF and HF variance signals.

10. The system of claim 8, wherein, when a ventricular rate smoothing or ventricular rate regulation is turned on to reduce variability in the ventricular heart rate, then the autonomic balance indicator operates to use the detecting the intrinsic atrial heart contractions for the providing the indication of the balance between sympathetic and parasympathetic components of the autonomic nervous system.

* * * * *

UNITED STATES PATENT AND TRADEMARK OFFICE
CERTIFICATE OF CORRECTION

PATENT NO. : 6,748,272 B2
DATED : June 8, 2004
INVENTOR(S) : Carlson et al.

It is certified that error appears in the above-identified patent and that said Letters Patent is hereby corrected as shown below:

Title page,
Item [56], References Cited, FOREIGN PATENT DOCUMENTS, after "8/2000" insert -- A61B --.
OTHER PUBLICATIONS,
"Behrens, S., et al.," reference, delete "Vererans" and insert -- Veterans --, therefor.

Column 13,
Line 31, after "for" delete "the".

Column 14,
Line 45, after "for" delete "the".

Signed and Sealed this

Fourth Day of January, 2005

JON W. DUDAS
*Director of the United States Patent and Trademark Office*